United States Patent
Winters et al.

(10) Patent No.: US 9,578,878 B2
(45) Date of Patent: Feb. 28, 2017

(54) ANTIMICROBIAL EFFICACY OF AN OREGANO OIL AND CAPRYLIC ACID BLEND

(71) Applicant: Kemin Industries, Inc., Des Moines, IA (US)

(72) Inventors: Megan Winters, Urbandale, IA (US); Satish Nayak, West Des Moines, IA (US)

(73) Assignee: Kemin Industries, Inc., Des Moines, IA (US)

( * ) Notice: Subject to any disclaimer, the term of this patent is extended or adjusted under 35 U.S.C. 154(b) by 0 days.

(21) Appl. No.: 14/621,717

(22) Filed: Feb. 13, 2015

(65) Prior Publication Data
US 2015/0230458 A1 Aug. 20, 2015

Related U.S. Application Data

(60) Provisional application No. 61/939,858, filed on Feb. 14, 2014.

(51) Int. Cl.
*A01N 37/02* (2006.01)
*A01N 31/08* (2006.01)

(52) U.S. Cl.
CPC ............... *A01N 37/02* (2013.01); *A01N 31/08* (2013.01)

(58) Field of Classification Search
None
See application file for complete search history.

(56) References Cited

U.S. PATENT DOCUMENTS

| 2,438,091 | A | 3/1948 | Lynch et al. |
| 2,658,072 | A | 12/1953 | Kosmin et al. |
| 5,573,709 | A | 11/1996 | Wells |
| 2,528,378 | A1 | 10/2015 | Mannheimer et al. |
| 2012/0219682 | A1 | 8/2012 | Monteleone et al. |
| 2012/0282207 | A1 | 11/2012 | Lutz |

FOREIGN PATENT DOCUMENTS

WO   WO 2010010320 A1   1/2010

OTHER PUBLICATIONS amazon.com, "BioActive Nutrients Oregano Oil 1oz. Bottle", Feb. 7, 2013.
Hulankova et al., "Inhibition of Listeria monocytogenes in minced beef by combined effect of oregano essential oil and caprylic acid", "Maso International BRNO", 2011, pp. 11-14, vol. 1, Published in: Czech Republic.

*Primary Examiner* — Samantha Shterengarts
(74) *Attorney, Agent, or Firm* — Davis, Brown, Koehn, Shors & Roberts, P.C.

(57) ABSTRACT

The purpose of this study was to test the efficacy of an oregano extract containing carvacrol and capyrlic acid blend by screening for inhibition and by conducting a preservative efficacy test, USP 51, in skin creams. Minimum inhibitory concentrations were found for *Escherichia coli, Staphylococcus aureus, Pseudomonsas aeruginosa, Streptococcus sanguinis, Salmonella enterica, Candida albicans,* and *Aspergillus brasiliensis.*

7 Claims, 4 Drawing Sheets

ANTIMICROBIAL EFFICACY OF AN OREGANO OIL AND CAPRYLIC ACID BLEND

This application claims priority to U.S. Patent Application Ser. No. 61/939,858, filed Feb. 14, 2014, which is incorporated herein in its entirety by this reference.

BACKGROUND OF THE INVENTION

The present invention relates generally to antimicrobials for personal care products and, more specifically, to a blend of oregano extract containing carvacrol and caprylic acid.

Consumer demand has shifted to the purchasing of personal care products with "all natural" ingredients. Manufacturers have answered the demand by changing existing formulations or by creating new ones.

For personal care formulators, no functional ingredient has been the most difficult to change than the preservative. Preservatives are necessary to maintain the stability of a formulation 1 to 2 years. Widely used preservatives are in the paraben class: methyl-, butyl-, propyl-, heptyl-, ethyl-. These compounds are highly efficacious on bacteria and fungi, but they have received negative attention in regards to being a possible cause of breast cancer. Some natural preservatives are on the market but have varying degrees of efficacy.

Studies have shown that carvacrol disrupts the membrane potential of bacteria, and recently a cultivar of oregano containing ≥5% of the molecule by dry weight of material has been developed. Oregano oil containing 94.6% carvacrol has been shown to be an effective disinfectant ingredient against bacteria, yeast, and mold when used at a 1.0% inclusion of carvacrol.

The purpose of this study was to test the efficacy of a carvacrol and caprylic acid blend first by finding screening for inhibition and then by conducting a preservative efficacy test, USP 51, in skin creams. This method requires a 1-3 log reduction after 14 days with no increase in growth after 28 days for *Escherichia coli, Staphylococcus aureus, Pseudomonas, aeruginosa, Candida albicans,* and *Aspergillus brasiliensis.*

SUMMARY OF THE INVENTION

A blend of an oregano extract containing high amounts of carvacrol is combined with caprylic acid to produce an antimicrobial particularly suited for use in personal care products. The composition meets the USP 51 preservative challenge test. Minimum inhibitory concentrations were found for *Escherichia coli, Staphylococcus aureus, Pseudomonsas aeruginosa, Streptococcus sanguinis, Salmonella enterica, Candida albicans,* and *Aspergillus brasiliensis.* The composition successfully reduced bacteria and yeast 5 log and mold 4 log in a cream formulation after 7 days. Caprylic acid was unable to reduce mold in the same amount of time.

DETAILED DESCRIPTION OF PREFERRED EMBODIMENTS

As used in this application, the following terms have the meanings set out below.

The amount of the active compounds carvacrol and caprylic acid to be used in the compositions according to the invention may be readily determined by a person skilled in the art, as a function of the nature of the compound used and/or the desired effect. In general, this amount may be between 0.001% and 10% by weight relative to the total weight of the composition, in particular between 0.01% and 5% by weight, preferably between 0.05% and 3% by weight, better still between 0.1% and 2% by weight and preferentially between 0.5% and 2% by weight. The volume ratio of carvacrol to caprylic acid inn compositions of the present invention may be between 1:100 and 100:1, in particular between 2:50 and 1:1, preferably between 1:25 and 1:2, better still between 1:15 and 2:15.

The compounds may be used in particular as a mixture in a composition which comprises a physiologically acceptable medium, in particular in a cosmetic or personal care composition which thus moreover comprises a cosmetically or pharmaceutically acceptable medium.

The physiologically acceptable medium in which the compounds according to the invention may be used, and the constituents thereof, the amount thereof, the presentation form of the composition and its method of preparation, may be chosen by a person skilled in the art on the basis of his general knowledge depending on the type of composition desired.

The present invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include, for example, an emulsion, a lip balm, a lip gloss, a lotion, a mask, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and the like, as well as other botanicals such as aloe, chamomile, and the like, and as further described below.

Cosmetically or dermatologically acceptable vehicles that can be used in the present topical compositions include, but are not limited to, one or more aqueous systems, glycerins, Cl-4 alcohols, fatty alcohols, fatty ethers, fatty esters, polyols, glycols, vegetable oils, mineral oils, liposomes, laminar lipid materials, silicone oils, water or any combinations thereof.

In the present invention, the vehicle may be in the form of an aqueous phase, an oil phase, a gel, a wax-in-water emulsion, a silicone-in-water emulsion, a water-in-silicone, an oil-in-water emulsion, or a water-in-oil emulsion. The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from 0.5 to 99.99 wt. % by weight of the composition.

When the composition of the invention is in the form of an emulsion, it can also optionally comprise a surfactant, preferably in an amount of from 0.1 to 30% and in particular from 1 to 20 wt. % by weight of the composition.

The composition can also comprise a thickening polymer such as an amphiphilic polyurethane, a polyacrylic homopolymer or copolymer, a polyester, and/or a hydrocarbon-based resin. The polymers can be dissolved or dispersed in the cosmetically acceptable vehicle and optionally combined with a plasticizer.

The composition of the invention may also comprise an oil phase containing oil soluble or oil dispersible ingredients that are liquid at room temperature (25° C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semi-solid at room temperature such as cyclomethicones and dimethicones, optionally comprising a phenyl group, for instance phenyl trimethicones, siloxanes, and mixtures thereof. These oils are usually present in an amount of 0 to about 90 wt. %, preferably from about 1 to 80 wt. % by weight of the oil phase.

The oil phase of the composition of the invention may also comprise one or more cosmetically acceptable organic solvents. These solvents are present in an amount of 0 to about 60 wt. %, preferably about 1 to 30 wt. % by weight of the composition and can be selected from the group consisting of lipophilic organic solvents, amphiphilic organic solvents and mixtures thereof. Suitable solvents which can be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 to 20 wt. % by weight of the composition. The nature of these ingredients and their amounts must be compatible with the production of the compositions of the invention.

The composition of the invention may also comprise an additional particulate phase, typically present in an amount of 0 to about 30 wt. % by weight of the composition, preferably from about 0.05 to 20 wt. %, and which can comprise pigments and/or pearlescent agents and/or fillers used in cosmetic compositions. Suitable inorganic pigments include titanium oxide, zirconium oxide and cerium oxide, as well as zinc oxide, iron oxide, chromium oxide and ferric blue. Suitable organic pigments include barium, strontium, calcium, and aluminum lakes and carbon black Suitable pearlescent agents include mica coated with titanium oxide, with iron oxide, or with natural pigment. Fillers are normally present in an amount of 0 to about 20 wt. % by weight of the composition, preferably about 0.1 to 10 wt. %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Corning), and silicone resin microbeads (Tospearl from Toshiba).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present invention may contain from 0 to about 20 wt. % waxes by weight of the composition. The gums are generally high molecular weight PDMSs or cellulose gums or polysaccharides and the semisolid materials are generally hydrocarbon-based compounds such as lanolins and derivatives thereof or alternatively PDMSs. The compositions of the present invention may contain from 0 to about 20 wt. % gums by weight of the composition, typically from about 0.1%. to 10 wt. %.

In another preferred embodiment, the topical compositions of the present invention also include at least one of the following: a skin penetration enhancer, a surface smoother, a skin plumper, an optical diffuser, a sunscreen, an exfoliation promoter, and an antioxidant. Details with respect to these and other suitable cosmetic ingredients can be found in the International Cosmetic Ingredient Dictionary and Handbook, 10th Edition (2004), published by the Cosmetic, Toiletry, and Fragrance Association (CTFA), at pp. 2177-2299, which is herein incorporated by reference in its entirety.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to 20% of the total weight of the composition.

Emulsifiers are typically present in emulsion compositions of the invention in an amount of about 0.1% to 30%, by weight and preferably from about 0.5% to 30% by weight relative to the total weight of the composition. However, not all compositions will necessarily include emulsifiers.

The antimicrobial compounds of the present invention can be formulated in various cosmetic and personal care consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, and balms.

The compositions that contain the compound of the present invention may also contain adjuvants which are used in the cosmetics field, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants may be those conventionally used in the field considered. These adjuvants, depending on their nature, can be introduced into the fatty phase, into the aqueous phase or into the lipid vesicles. In addition, moisturizers may complete the effect obtained using the sapogenins according to the invention and anti-inflammatory agents are also useful.

Additional cosmetically or pharmaceutically beneficial ingredients can also be included in the formulated compositions of the present invention, which can be selected from skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about C10 to C22, long chain fatty amines from about C10 to C22, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, crosslinked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, *psyllium* seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface-active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated C12-38 n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL as described in U.S. Pat. No. 2,528,378. Other sarcosinates and sarcosinate derivatives that can be found in the CTFA Cosmetic Ingredient Handbook, Fifth Edition, 1988, are incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowedimonium chloride, hydroxycetyl hydroxyethyl dimonium chloride, hydroxyethyl behenamidopropyl dimonium chloride, hydroxyethyl cetyldimonium chloride, hydroxyethyl tallowedimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; quaternium-16; quaternium-18, lauralkonium chloride, olealkmonium chloride, cetylpyridinium chloride, polyquaternium-5, polyquaternium-6, polyquaternium-7, polyquaternium-10, polyquaternium-22, polyquaternium-37, polyquaternium-39, polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions that contain the antimicrobial compounds of the present invention may include long chain fatty amines from about C10 to C22 and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of C10 to C32, preferably C14 to C22, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH.sub.2).sub.3 radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable compositions that contain the antimicrobial compounds of the present invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable compositions that contain the antimicrobial compounds of the present invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, C12 to C16 fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions that contain the antimicrobial compounds of the present invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end-blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions that contain the antimicrobial compounds of the present invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane. 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions that contain the antimicrobial compounds of the present invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the present invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions that contain the antimicrobial compounds of the present invention may include volatile hydrocarbon oils. The volatile hydrocarbon comprises from about C-6 to C-22 atoms. A preferred volatile hydrocarbon is an aliphatic hydrocarbon having a chain length from about C-6 to C-16 carbon atoms. An example of such compound includes isohexadecane, under the trade name Permethyl 101A, available from Presperse, South Plainfield, N.J., USA. Another example of a preferred volatile hydrocarbon is C-12 to C-14 isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions that contain the antimicrobial compounds of the present invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. Specific examples, using the CTFA designation, include, but are not limited to polyquaternium-10, guar hydroxypropyltrimonium chloride, starch hydroxypropyltrimonium chloride, polyquaternium-4, polyquaternium-5, polyquaternium-6, polyquaternium-7, polyquaternium-14, polyquaternium-15, polyquaternium-22, polyquaternium-24, polyquaternium-28, polyquaternium-32, polyquaternium-33, polyquaternium-36, polyquaternium-37, polyquaternium-39, polyquaternium-45, polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable compositions that contain the antimicrobial compounds of the present invention may include one or more rheological modifiers. The rheological modifiers that can be used in this invention include, but are not limited to high molecular weight crosslinked homopolymers of acrylic acid, and acrylates/C10-30 alkyl acrylate crosspolymer, such as the Carbopol and Pemulen series, both available from B.F. Goodrich, Akron, Ohio, USA; anionic acrylate polymers such as Salcare and cationic acrylate polymers such as Salcare SC96, available from Ciba Specialties, High Point, N.C., USA; Acrylamidopropylttrimonium chloride/acrylamide; hydroxyethyl methacrylates polymers, Steareth-10 allyl ether/acrylate copolymer; acrylates/beheneth-25 metacrylate copolymer, known as Aculyn, available from International Specialties, Wayne, N.J., USA; Glyceryl Polymethacrylate, Acrylates/Steareth-20 methacrylate copolymer; bentonite; gums such as alginates, carageenans, gum *acacia*, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition that contain the antimicrobial compounds of the present invention may include one or more antioxidants, which include, but are not limited to ascorbic acid, BHT, BHA, erythorbic acid, bisulfite, thioglycolate, tocopherol, sodium metabisulfite, vitamin E acetate, and sugar palmitate. The antioxidants will be present at from 0.01 to 5 weight percent, preferably 0.1 to 3 weight percent and most preferably from 0.2 to 2 weight percent of the cosmetically acceptable composition.

The cosmetically acceptable compositions that contain the antimicrobial compounds of the present invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl)aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable compositions that contain the antimicrobial compounds of the present invention may include one or more preservatives. Example of preservatives, which may be used include, but are not limited to 1,2-dibromo-2,4-dicyano butane (methyldibromo glutaronitrile, known as MERGUARD. Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, and sodium benzoate, and mixtures thereof.

The cosmetically acceptable compositions that contain the antimicrobial compounds of the present invention can be presented in various forms. Examples of such forms include, but are not limited a solution, liquid, cream, emulsion, dispersion, gel, and thickening lotion.

The cosmetically acceptable compositions that contain the antimicrobial compounds of the present invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable compositions that contain the antimicrobial compounds of the present invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable compositions that contain the antimicrobial compounds of the present invention can also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin that contain the antimicrobial compounds of the present invention include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

If the compositions that contain the antimicrobial compounds of the present invention are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

The cosmetically acceptable carrier contained in the cosmetic compositions that contain the antimicrobial compounds of the present invention may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solutions and emulsions that contain the antimicrobial compounds of the present invention may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension that contain the antimicrobial compounds of the present invention may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these ingredients.

The term "effective dose" or "effective amount" refers to an amount effective, at dosages and for periods of time necessary, to achieve the desired result. The effective amount of compositions of the invention may vary according to factors such as the composition or formulation of the product being treated with the compositions of the present invention.

In preferred embodiments of the present invention, the effective amount of a blend of carvacrol and caprylic acid ranges from 0.001% and 10% by weight of the products being treated and all values between such limits, including, for example, without limitation or exception, 0.002%, 0.104%, 0.132%, 0.217%, 0.336%, 0.489%, 1.377%, 4.332%, 5.023% and 8.990%. Stated another way, in preferred embodiments of the invention, the dosage can take any value "ab.cde" % wherein a is selected from the numerals 0 and 1, and b, c, d and e are each individually selected from the numerals 0, 1, 2, 3, 4, 5, 6, 7, 8 and 9, with the exception that e cannot be less than 1 if a, b, c and d are all 0.

Where ranges are used in this disclosure, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3. 6.3, 0.815 and so forth) are included as are all intermediate ranges (e.g., 0.2-0.5, 0.54-0.913, and so forth).

Example 1

Materials and Methods

Preparation of Treatments.

Oregano essential oil containing 94.6% carvacrol was acquired internally and octanoic acid (caprylic acid) was obtained from Sigma-Aldrich. A 10% carvacrol solution was prepared in caprylic acid by a volume by volume basis into a glass container. The solution was mixed thoroughly by a vortex mixer until a clear, homogenous mix was obtained. The percentage of this treatment used in the study was the dose of the mixture in its entirety and not by the inclusion of carvacrol.

For assays to find minimum inhibitory concentrations, all treatments were diluted in 10% DMSO and 0.5% Tween 80 to stabilize the samples.

Preparation of Inoculum for Minimum Inhibitory Studies.

Microorganisms *Escherichia coli* (ATCC #8739), *Streptococcus sanguinis* (ATCC #BAA-1455), *Salmonella enterica* subsp. *enterica* (ex Kauffmann and Edwards) Le Minor and Popoff serovar *Typhimurium* (ATCC #14028), *Staphylococcus aureus* (ATCC #6538), *Pseudomonas aeruginosa* (ATCC #9027), and *Candida albicans* (ATCC #10231) were obtained from a −80° C. internal stock culture. *Aspergillus brasiliensis* (ATCC #16404) was obtained from an internal stock solution culture stored at 4° C. *E. coli, S. enterica S. aureus*, and *P. aeruginosa* were grown in tryptic soy broth (TSB) and incubated at 37° C. for 24 h. *S. sanguinis* was grown in brain heart infusion broth (BHI). *A. brasiliensis* was plated on Sabourand dextrose agar (SDA) and incubated at 25° C. for 5-7 days. *C. albicans* was grown in Sabourand dextrose broth (SDB) and incubated at 25° C. for 48 h.

*A. brasiliensis* was harvested by adding 18 mL sterile saline to the plate and agitating the mold from the agar with a sterile inoculating loop. The inoculum was collected upon agitation. All suspended microbes were diluted with the same type of broth media used to grow each organism until an inoculum in the range of $10^6$ CFU/mL was achieved. The inoculum concentration was determined by plate count method. Each strain was identified by plating on the appropriate growth media, *E. coli, S. aureus*, and *P. aeruginosa* on tryptic soy agar (Bacto, BD Sciences, Manassas, Va.) and *C. albicans* and *A. brasiliensis* on Sabrouand dextrose agar, to ensure there was no contamination of the inoculum.

Microtiter Assay. A microtiter assay was completed *E. coli, S. aureus, P. aeruginosa, S. enteria, S. sanguinis*, and *C. albicans*. Briefly, $10^6$ cfu/ml preparations of each organism were made and enumerated using a Petroff-Hausser counting chamber. A 100 µl aliquot of the inoculums was dispensed into microtiter plate wells and a 100 µl aliquot of treatment was dispensed into the same wells. Two separate set of wells were prepared as positive and negative controls, with the positive wells containing 100 µl test organism in growth media and 100 µl sterile phosphate buffer and with the negative control wells containing 100 µl of the same growth media and 100 µl sterile phosphate buffer. The plates were incubated overnight at the appropriate temperature for each organism. A plate reader was used to track the kinetic growth curve using 405 nm and 620 mm. The last time point at 24 hours was averaged and used to determine $MIC_{90}$. Each treatment was conducted in triplicate wells.

Zone of Inhibition Assay.

A zone of inhibition assay was used for *A. brasiliensis* and *C. albicans*. SDA was used as the plated medium. Inocula at $10^5$ cfu/ml were prepared and counted using a Petroff-Hausser counting chamber. The diameter of no growth around a 6 mm blank disk after incubation at 25° C. for 72 hrs was compared to the untreated control. 20 µL of treatment was applied to each disk in triplicate. 10% DMSO was used as the control.

Poison Agar Assay.

A poison agar assay was completed for *A. brasiliensis*. Potato dextrose agar was used as the plated medium. Inocula at $10^5$ cfu/ml were prepared and counted using a Petroff-Hausser counting chamber. Each treatment was added directly into the control without DMSO and Tween 80 as used in the previous experiments. The diameter of no growth around a 6 mm blank disk after incubation at 25° C. for 72 hrs was compared to the untreated control.

Preparation of Cold Process Creams.

Creams were prepared aseptically by spraying 70% isopropyl alcohol on all surfaces and labware. Carbomer 940 and coco caprylate were obtained from BPI Labs, Inc. (Evanston, Wyo.). Safflower and olive oils were purchased from Jedwards International, Inc. (Quincy, Mass.). The cream formulations were as follows:

TABLE 1

Percentage of ingredients used to prepare cold process cream.

| Ingredients | Negative Control A, B & 1, 2 | Treatment A | Treatment B | Treatment 1 | Treatment 2 | Positive Control A, B | Positive Control 1, 2 |
|---|---|---|---|---|---|---|---|
| Water Phase | | | | | | | |
| DI water | Up to 100 | Up to 100 | Up to 100 | Up to 100 | Up to 00 | Up to 100 | Up to 100 |
| Carbomer 940 | 0.5 | 0.5 | 0.5 | 0.5 | 0.5 | 0.5 | 0.5 |

TABLE 1-continued

Percentage of ingredients used to prepare cold process cream.

| Ingredients | Negative Control A, B & 1, 2 | Treatment A | Treatment B | Treatment 1 | Treatment 2 | Positive Control A, B | Positive Control 1, 2 |
|---|---|---|---|---|---|---|---|
| Glycerin | 3.0 | 3.0 | 3.0 | 3.0 | 3.0 | 3.0 | 3.0 |
| Lysofix | 3.5 | 3.5 | 3.5 | 3.5 | 3.5 | 3.5 | 3.5 |
| Oil Phase | | | | | | | |
| Olive oil | 6.0 | 6.0 | 6.0 | 6.0 | 6.0 | 6.0 | 6.0 |
| Coco caprylate | 2.0 | 2.0 | 2.0 | 2.0 | 2.0 | 2.0 | 2.0 |
| Optiphen | 0 | 0 | 0 | 0 | 0 | 1.0 | 0 |
| Euxyl PE9010 | 0 | 0 | 0 | 0 | 0 | 0 | 1.0 |
| 10% Carvacrol in Capyrlic Acid | 0 | 0 | 0 | 0.5 | 1.0 | 0 | 0 |
| Caprylic Acid | 0 | 0.5 | 1.0 | 0 | 0 | 0 | 0 |

Preservative studies were completed at different times for caprylic acid and 10% carvacrol in caprylic acid. The negative and positive controls were designated at A, B for the caprylic acid study and 1, 2 for the addition of carvacrol in Table 1. The change in positive control ingredients was due to a shift in the preservative used for regular KPC formulations.

DI water was added to a pre-weighed 250 mL beaker and mixed at 800 rpm using an overhead mixer (Eurostar power-b IKA-WERKE, Wilmington, N.C.) with a 3 blade SIZE impeller. Carbomer 940 was slowly added to the center of the mixing water. The mixture was hydrated for 30 minutes while covered with aluminum foil. Glycerin quickly followed by Lysofix were slowly added to the solution. After 2 minutes, safflower oil, olive oil, and coco caprylate were slowly added to the mixture at 1000 rpm. The solution was mixed for 30 minutes while covered with aluminum foil. Next the pH was measured and adjusted to 5.5 with a 33.3% sodium hydroxide solution. The mixing speed was increased to 1400 rpm. From time to time, it was necessary to scrape the sides of the beaker with a spatula to ensure that the cream became homogenized. When the cream appeared homogenized, the amount of preservative or treatment was added. After 2 minutes, the cream was weighed and water added to reach a mass balance.

Preparation of Inoculum for Preservative Efficacy Study.

Microorganisms *Escherichia coli* (ATCC #8739), *Staphylococcus aureus* (ATCC #6538), *Pseudomonas aeruginosa* (ATCC #9027), and *Candida albicans* (ATCC #10231) were obtained from a −80° C. internal stock culture. *Aspergillus brasiliensis* (ATCC #16404) was obtained from an internal stock solution cultured stored at 4° C. *E. coli, S. aureus*, and *P. aeruginosa* were grown in tryptic soy broth (Bacto, BD Sciences, Manassas, Va.) and incubated at 37° C. for 24 h. *A. brasiliensis* was plated on Sabourand dextrose agar (Bacto, BD Sciences, Manassas, Va.) and incubated at 25° C. for 5-7 days. *C. albicans* was grown in Sabourand dextrose broth (Bacto, BD Sciences, Manassas, Va.) and incubated at 25° C. for 48 h.

Pathogens in broth were harvested by centrifugation (2400 rpm, 20 minutes) and suspended in sterile saline. *A. brasiliensis* was harvested by adding 18 mL sterile saline to the plate and agitating the mold from the agar with a sterile inoculating loop. The inoculum was collected upon agitation. All suspended microbes were diluted with sterile saline until an inoculum in the range of $10^8$ CFU/mL was achieved. The inoculum concentration was determined by plate count method. Each strain was identified by plating on the appropriate growth media, *E. coli, S. aureus*, and *P. aeruginosa* on tryptic soy agar (Bacto, BD Sciences, Manassas, Va.) and *C. albicans* and *A. brasiliensis* on Sabrouand dextrose agar, to ensure there was no contamination of the inoculum.

Preservative Efficacy Testing.

Creams were plated according to the SOP[1] to ensure they were sterile. Each prepared cream was inoculated with 0.1 mL of inoculum per 10 g of sample to reach the targeted inoculated concentration of 6-log cfu/g. Samples were vortexed for 2 minutes. The inoculated creams were incubated at 25° C. The samples were enumerated on days 0, 2, 3, 7, 14, and 28 by diluting 1 g of sample with sterile saline and plating in duplicate on the inoculated organism's appropriate growth media. Plate count method was used to determine the number of CFU/g.

Calculations of the Results.

The plate counts obtained each day were averaged for each treatment. The results were shown graphically by the log count of each averaged value per treatment per day. For any values that were too numerous to count (TNTC), the previous enumeration value was used, and for plates that had no growth, the lowest dilution plated was recorded.

Results

Inhibitory Assays. The $MIC_{90}$ for each organism is presented in Table 2. For *P. aeruginosa* and *S. enterica*, a lower MIC was observed for the combination mixture than when caprylic acid is used alone. *E. coli, S. aureus, S. sanguinis*, and *C. albicans* were sensitive to caprylic acid. In the zone of inhibition assay in Table 3, similar sensitivity is observed for *C. albicans*, but *A. brasiliensis* shows sensitivity only to the combination. Table 4 shows the results from the poison agar assay. In this assay, the $MIC_{90}$ for each treatment was as follows: carvacrol—0.03%, caprylic acid—0.09%, and carvacrol/caprylic acid—0.10%.

TABLE 2

Minimum inhibitory concentrations (MIC) to inhibit 90% growth.

Minimum Inhibitory Concentration (MIC) n = 3

| | E. coli | S. aureus | P. aeruginosa | S. enterica | S. sanguinis | C. albicans |
|---|---|---|---|---|---|---|
| Carvacrol/Caprylic Acid | 0.30% | 0.10% | 0.50% | 0.50% | 0.10% | 0.10% |
| Caprylic Acid | 0.27% | 0.09% | 0.90% | 0.90% | 0.09% | 0.09% |
| Carvacrol | 0.10% | 0.05% | >0.1% | 0.05% | 0.05% | 0.10% |

TABLE 3

Inhibition diameters on yeast and mold from the zone of inhibition assay.

| | Inhibition Diameter (mm) (n = 3) | |
|---|---|---|
| Sample | C. albicans | A. brasiliensis |
| 10% DMSO (control) | 0 | 0 |
| 0.3% Caprylic Acid/Carvacrol | 0 | |
| 0.5% Caprylic Acid/Carvacrol | 7 | |
| 1.0% Caprylic Acid/Carvacrol | 10.5 | 6 |
| 3.0% Caprylic Acid/Carvacrol | 26.5 | 13.5 |
| 5.0% Caprylic Acid/Carvacrol | | 21.5 |
| 0.45% Caprylic Acid | 3.5 | |
| 0.9% Caprylic Acid | 4.5 | 0 |
| 2.7% Caprylic Acid | 24.5 | 0 |
| 4.5% Caprylic Acid | | 0 |

TABLE 4

Growth diameters of A. brasiliensis from the poison agar assay.

| Treatment | Diameter of Growth (mm) | % Inhibition from Control |
|---|---|---|
| Untreated Control | 7.65 | N/A |
| 0.005% Carvacrol | 6.50 | 15.10 |
| 0.010% Carvacrol | 2.70 | 64.70 |
| 0.030% Carvacrol | 0.00 | 100.00 |
| 0.045% Capryllic Acid | 5.00 | 34.60 |
| 0.090% Caprylic Acid | 0.00 | 100.00 |
| 0.270% Caprylic Acid | 0.00 | 100.00 |
| 0.050% Carvacrol/Caprylic Acid | 3.75 | 51.00 |
| 0.100% Carvacrol/Caprylic Acid | 0.00 | 100.00 |
| 0.300% Carvacrol/Caprylic Acid | 0.00 | 100.00 |

PET on Caprylic Acid.

Figure 1:
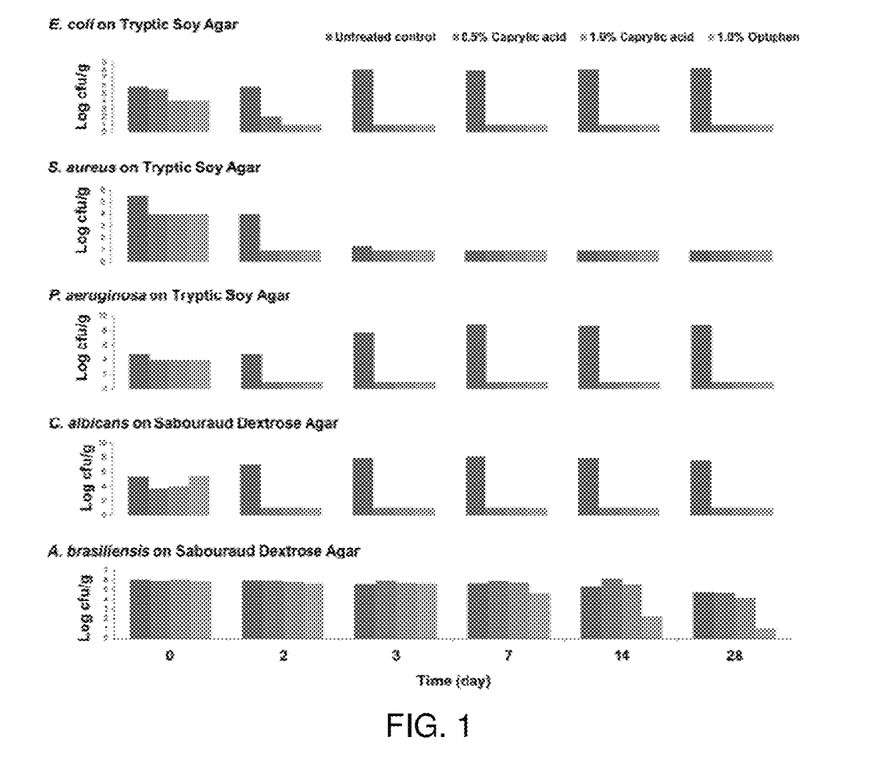
FIG. 1 is a chart of log counts of USP 51 over 28 days for untreated control, 0.5% caprylic acid, 1.0% caprylic acid, and 1.0% Optiphen.
Figure 2:
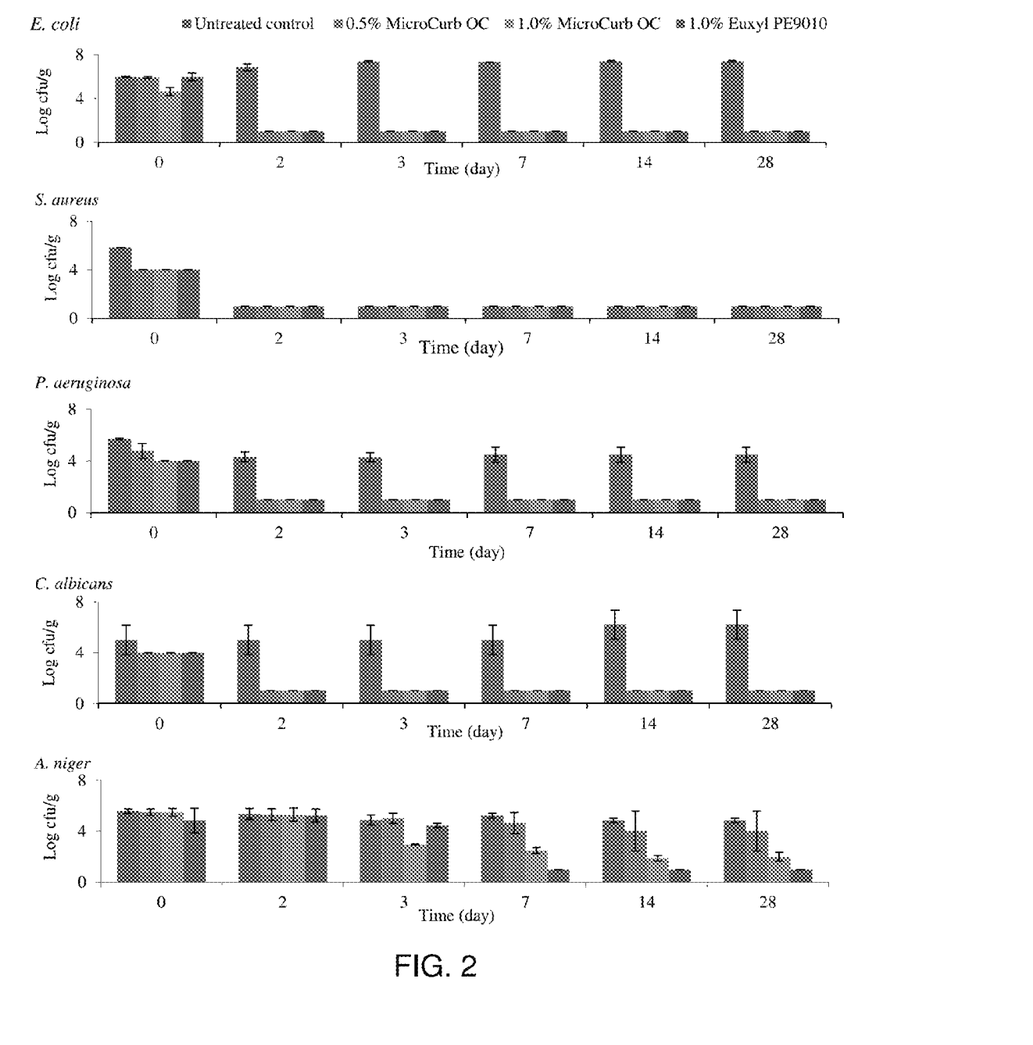
FIG. 2 is a chart of log counts of USP 51 over 28 days for untreated control, 0.5% caprylic acid/carvacrol, 1.0% caprylic acid/carvacrol, and 1.0% Euxyl PE 9010.

The results for the preservative efficacy test using caprylic acid are shown in FIG. 1. *S. aureus, P. aeruginosa*, and *C. albicans* were reduced by 5 Log after 2 days, and *E. coli* reduced by 5 log after 3 days. The untreated control reduced *S. aureus* 5 Log after 3 days. *A. brasiliensis* reduced 2 Log by the end of the study for treatments containing caprylic acid, and the Optiphen PET on 10% Carvacrol in Caprylic Acid. The results for the preservative efficacy test using 10% carvacrol in caprylic acid are shown in FIG. 2. *E. coli, S. aureus, P. aeruginosa*, and *C. albicans* were reduced 5 log after 2 days. *A. brasiliensis* was reduced 4 log after 7 days and remained at that level throughout the 28-day study period.

Discussion

Caprylic acid on its own possesses considerable antibacterial properties, but as seen in the PET results, it possesses little effect on mold in formulation. The addition of carvacrol to the formulation substantially impacted the growth of mold when a 10% carvacrol in caprylic acid solution was included at 1.0%. The results obtained in the PET study prove that there is an added effect of the oregano oil in caprylic acid on mold. The added effect was also seen in the difference of MICs for the combination and caprylic acid found for *P. aerugionsa* and *S. enterica* and in the zone of inhibition study. With very little effective, natural preservatives for cosmetics on the market, the combination of carvacrol and caprylic acid would fill a gap customers are striving to fill.

Example 2

The purpose of this study was to test the preservation efficacy of MicroCurb OC in a cream formulation. In this study, skin cream formulations were challenged with five microorganisms and the change in the microbial count was evaluated over a 28-day period. MicroCurb OC was able to reduce the bacteria and yeast by 5-log within two days and the mold (*Aspergillus brasiliensis*) by 3.5-log within 14 days, which met the requirements stated in USP <51>: antimicrobial effectiveness testing (United States Pharmacopeia. USP <51>. Antimicrobial effectiveness testing. Rockville, Md.). These data illustrate that MicroCurb OC is a powerful natural preservative for personal care formulations. As a control, caprylic acid alone was also tested, although able to reduce bacteria and yeast, it was unable to reduce the mold.

Materials and Methods

Materials.

Oregano essential oil containing 67.8% carvacrol (lot number 628034, thymol was not detectable) was received from Kemin SCI. Caprylic acid was obtained from Fisher Scientific (catalog number AC12939). To make MicroCurb OC, a blend with 10% oregano essential oil and 90% caprylic acid (w/w) was prepared for initial testing. The solution was mixed thoroughly for 10 seconds by a vortex mixer until a clear, homogenous mixture was obtained, resulting in the product MicroCurb OC.

Carbomer 940 and coco caprylate were obtained from BPI Labs, Inc. (Evanston, Wyo.). Safflower and olive oils were purchased from Jedwards International, Inc. (Quincy, Mass.). Lysofix lot number 1312102985 was obtained in-house. Ultra filtered de-ionized water was obtained from Kemin Health R&D. Glycerin was obtained from KFT production, lot number 1310108120. Euxyl PE9010 was obtained from Schiilke (Fairfield, N.J.) and Optiphen were obtained from the Herbarie (Prosperity, S.C.). Sodium Hydroxide was obtained from Sigma-Aldrich (catalog number S5881). Tryptic soy agar (TSA cat. No. 211043), tryptic soy broth (TSB cat. No. 211825), sabourand dextrose agar (SDA cat. No. 211584), and sabourand dextrose broth (SDB cat. No. 238230) were obtained from BD Sciences (Manassas, Va.).

Preparation of Cold Process Creams.

Creams were prepared aseptically by spraying 70% isopropyl alcohol on all surfaces and glassware. Preservative studies were completed at different times for caprylic acid alone (Study 1) and MicroCurb OC (Study 2). Tables 5 and 6 list the various ingredients and their percentages used in Study 1 and 2, respectively.

TABLE 5

Base cream formulations for Study 1 and 2.

| Ingredients | Composition (%) |
|---|---|
| Water Phase | |
| Water | 73-74 |
| Carbomer 940 | 0.5 |
| Glycerin | 3.0 |
| Lysofix | 3.5 |
| Oil Phase | |
| Safflower oil | 12.0 |
| Olive oil | 6.0 |
| Coco caprylate | 2.0 |
| preservative | See Table 6 |

TABLE 6

List of preservatives used in the Study 1 and 2.

| Composition, %/Sample | Caprylic Acid (%) | Micro-Curb OC (%) | Optiphen (%) | Euxyl PE9010 (%) |
|---|---|---|---|---|
| Negative Control | — | — | — | — |
| Positive Control 1 | — | — | 1.0 | — |
| Positive Control 2 | — | — | — | 1.0 |
| 0.5% Caprylic acid | 0.5 | — | — | — |
| 1.0% Caprylic acid | 1.0 | — | — | — |
| 0.5% MicroCurb OC | — | 0.5 | — | — |
| 1.0% MicroCurb OC | — | 1.0 | — | — |

De-ionized water was added to a pre-weighed 250 mL beaker and mixed at 800 rpm using an overhead mixer (Eurostar power-b IKA-WERKE, Wilmington, N.C.) with a 3 blade impeller. Carbomer 940 was slowly added to the center of the mixing water. The mixture was hydrated for 30 minutes while covered with aluminum foil. Glycerin and Lysofix were slowly added to the solution. After solution appeared homogenous, safflower oil, olive oil, and coco caprylate were slowly added to the mixture at 1000 rpm. The solution was mixed for 30 minutes while covered with aluminum foil. Next the pH was measured (around 3.2) and adjusted to 5.5 with a 33.3% sodium hydroxide solution. The mixing speed was increased to 1400 rpm. From time to time, it was necessary to scrape the sides of the beaker with a spatula to ensure that the cream became homogenized. When the cream appeared homogenized, the preservative treatments listed in Tables 5 and 6 were added. After 5 minutes, the cream was weighed and water was replenished for the mass lost during the processing.

Preparation of Inoculum.

Microorganisms *Escherichia coli* (ATCC #8739), *Staphylococcus aureus* (ATCC #6538), *Pseudomonas aeruginosa* (ATCC #9027), and *Candida albicans* (ATCC #10231) were obtained from −80° C. internal stock cultures. *Aspergillus brasiliensis* (ATCC #16404) was obtained from an internal stock solution stored at 4° C. *E. coli, S. aureus,* and *P. aeruginosa* were grown in TSB and incubated at 37° C. for 24 h. *A. brasiliensis* was plated on SDA and incubated at 25° C. for 5-7 days. *C. albicans* was grown in SDB and incubated at 25° C. for 48 h.

Pathogens in broth were harvested by centrifugation (2400 rpm, 20 minutes) and suspended in sterile phosphate buffer. *A. brasiliensis* was harvested by adding 18 mL sterile phosphate buffer to the plate and agitating the mold from the agar with a sterile inoculating loop. The spores were collected upon agitation. All suspended microbes were diluted with sterile phosphate buffer until a concentration in the range of $10^8$ CFU/mL was achieved. The concentration was determined by plate count method. Each strain was identified by plating on the appropriate growth media, *E. coli, S. aureus,* and *P. aeruginosa* on TSA and *C. albicans* and *A. brasiliensis* on SDA, to ensure there was no contamination of the inoculum.

Preservative Efficacy Testing. Each tube was inoculated with the standardized microbial suspensions, using a ratio of 1 mL to 10 grams of the product, ensuring that the inoculum after suspension would yield the target level of 6-log CFU/g cream. For every testing time point, the sample was enumerated by sampling 1 g from the original product containers, serial dilution, and streaking plates containing the appropriate growth media to test colonization in duplicate. The inoculated plates were incubated at 25° C. for *C. albicans* and *A. niger* and 37° C. for *E. coli, S. aureus,* and *P. aeruginosa*. The number of viable microorganisms per gram was calculated via plate count method. The samples were enumerated on day 0, 2, 3, 5, 7, 14, and 28.

Calculations of the Results.

The plate counts obtained each day were averaged for each treatment. The results were shown graphically by the log count of each averaged value per treatment per day. For plates that had no growth, the lowest dilution plated was recorded.

Results

Preservative Efficacy Testing of Caprylic Acid (Study1).

Figure 3:
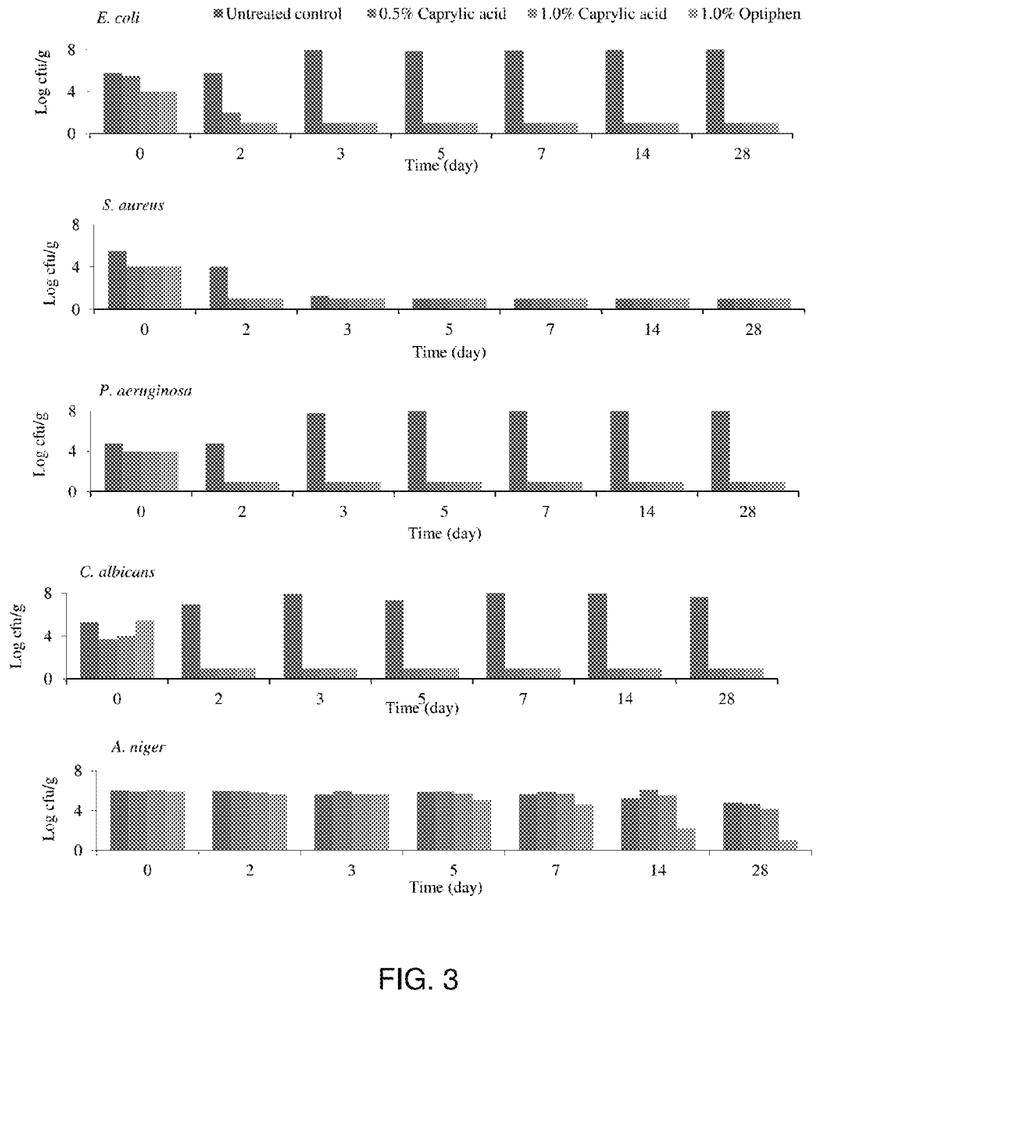
FIG. 3 is a chart showing the change in viable counts of microbes in formulations treated with different preservatives over the 28-day test period (Study 1); each bar is an average of two measurements.

The results for the preservative efficacy test using caprylic acid are shown in FIG. 3. *S. aureus, P. aeruginosa,* and *C. albicans* were reduced by 5-log after 2 days, and *E. coli* was reduced by 5-log after 3 days. *S. aureus* decreased in the untreated and treated samples over the test period. *A. brasiliensis* was reduced by 2-log by the end of the study for treatments containing caprylic acid, and by 5-log for the treatment with Optiphen.

Preservative Efficacy Testing of MicroCurb OC (Study 2).

Figure 4:
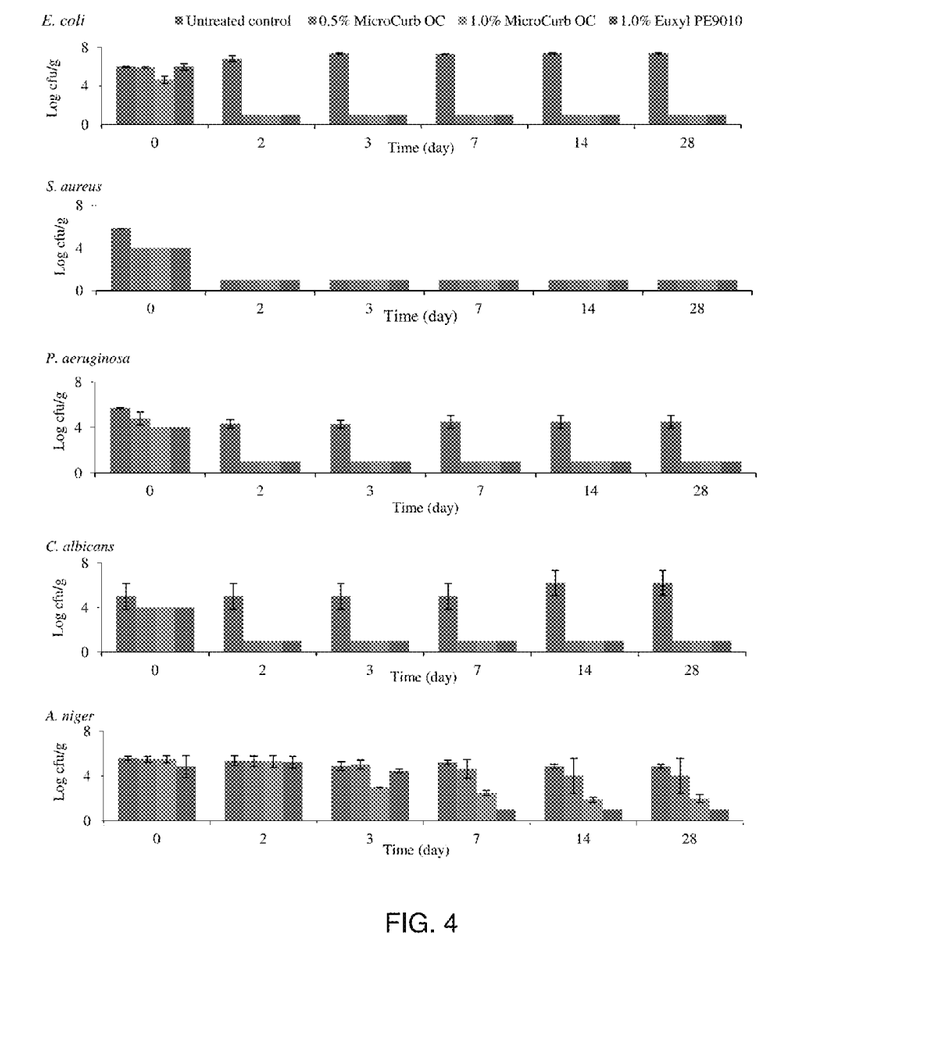
FIG. 4 is a chart of the change in viable counts of microbes in formulations treated with different preservatives over the 28-day test period (Study 2); each bar is an average of two measurements from two separate replicates; error bars denote one standard deviation from the average.

For MicroCurb OC the study was repeated twice. FIG. 4 illustrates the study results for the two replicates. MicroCurb OC was able to reduce *E. coli, S. aureus, P. aeruginosa* and *C. albicans* by 5-log within two days for the two tested concentrations. For *A. niger*, 3.5-log reduction by day 14 for the 1.0% inclusion of MicroCurb OC was observed. At 0.5% MicroCurb OC inclusion, the treatment was not consistently effective against *A. niger* in the two replicates and hence this concentration can be considered below the efficacious concentration to have a broad spectrum efficacy.

Discussion

A blend of caprylic acid and steam-distilled extract of the Hi-carvacrol line of oregano was developed. This extract, MicroCurb OC, was tested in a preservative efficacy challenge test in a skin cream formulation. Caprylic acid on its own possesses considerable antibacterial properties, but as seen in study 1, FIG. 1, it had little effect on mold in formulation. The addition of oregano extract to caprylic acid substantially impacted the growth of mold. At 1.0% inclusion, 3.5-log reduction was observed in *A. brasiliensis* by day 14. The results obtained in the PET study prove that there is a synergistic effect of the oregano oil in caprylic acid on mold. With very few effective, broad spectrum natural preservatives for cosmetics on the market, the combination of carvacrol and caprylic acid would fit well to fill that gap. Future studies would involve testing blends with other acceptable ingredients and also conducting the challenge study in other applications such as surfactant based shampoos.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A personal care product ingredient comprising a composition wherein the composition comprises an effective amount of caprylic acid and extract of oregano containing carvacrol that results in antimicrobial activity within a personal care product and further increases the shelf life of the personal care product.

2. The personal care product of claim 1, wherein the weight ratio of carvacrol to caprylic acid is between 1:100 and 1:1.

3. The personal care product of claim 1, wherein the personal care product is a lotion, moisturizer, or skin cream.

4. The personal care product ingredient of claim 1, wherein the effective amount inhibits the growth of mold and/or fungus.

5. The personal care product ingredient of claim 1, wherein the personal care product is applied topically to the skin.

6. A method of reducing microbial loads in a topical personal care product, comprising the step of adding an effective amount of a personal care product ingredient comprising a composition wherein the composition comprises an effective amount of caprylic acid and an extract of oregano containing carvacrol that reduces microbial loads within a personal care product and further increases the shelf life of the personal care product.

7. A method of protecting a topical personal care product against microbial contamination, comprising the step of adding an effective amount of a personal care product ingredient comprising a composition wherein the composition comprises an effective amount of caprylic acid and an extract of oregano containing carvacrol that reduces microbial contamination within a personal care product and further increases the shelf life of the personal care product.

* * * * *